United States Patent [19]

Cain

[11] 4,315,739
[45] * Feb. 16, 1982

[54] SPRING TENSIONING DEVICE AND METHOD

[76] Inventor: Steve B. Cain, 11006 N.W. 58, Kansas City, Mo. 64152

[ * ] Notice: The portion of the term of this patent subsequent to Apr. 29, 1997, has been disclaimed.

[21] Appl. No.: 105,286

[22] Filed: Dec. 19, 1979

Related U.S. Application Data

[63] Continuation-in-part of Ser. No. 796,987, May 16, 1977, Pat. No. 4,199,865.

[51] Int. Cl.³ ............................................... A61C 3/00
[52] U.S. Cl. ....................................... 433/21; 267/168
[58] Field of Search ......................... 433/21, 22, 20, 19, 433/18, 5; 267/168, 166, 179

[56] References Cited

U.S. PATENT DOCUMENTS

| | | | |
|---|---|---|---|
| 1,199,663 | 9/1916 | Canning | 433/23 |
| 1,202,797 | 10/1916 | Canning | 433/23 |
| 1,202,798 | 10/1916 | Canning | 433/21 |
| 1,452,436 | 4/1923 | Pullin | 267/168 |
| 3,011,775 | 12/1961 | MacLeod | 267/168 |
| 3,618,214 | 11/1971 | Armstrong | 433/21 |
| 3,936,938 | 2/1976 | Northcutt | 433/21 |
| 4,054,996 | 10/1977 | Wallshein | 433/7 |
| 4,091,540 | 5/1978 | Wallshein | 433/21 |
| 4,199,865 | 4/1980 | Cain | 433/21 |
| 4,215,983 | 8/1980 | Frazier | 433/5 |

FOREIGN PATENT DOCUMENTS

| | | | |
|---|---|---|---|
| 667040 | 10/1938 | Fed. Rep. of Germany | 433/20 |
| 2311225 | 12/1976 | France | 267/168 |

*Primary Examiner*—Robert Peshock
*Assistant Examiner*—John J. Wilson
*Attorney, Agent, or Firm*—Lowe, Kokjer, Kircher, Wharton & Bowman

[57] ABSTRACT

The present invention encompasses a novel spring construction and a method of application of the spring in the field of orthodontics. A tension spring member is at least partially surrounded by a tension releasable component of larger diameter. The tension spring will normally be a coil spring adapted to be placed under tension between two points. The tension releasable component will normally comprise either a closed coil spring or an open coil spring. In either case, the tension releasable portion comprises an integral extension of the tension spring member and is designed to deform in response to a predetermined force thereby releasing the device from its tension exerting position. The orthodontic method of the invention comprises anchoring one end of the novel tensioning device to a tooth to be moved and the other end to an anchor point. The device is then placed under tension and the tension releasable means is used to hold one end of the device.

18 Claims, 6 Drawing Figures

SPRING TENSIONING DEVICE AND METHOD

BRIEF DESCRIPTION OF THE INVENTION

This application is a continuation-in-part application of Ser. No. 796,987, entitled "Orthodontic Spring Appliance and Assembly", filed May 16, 1977, now U.S. Pat. No. 4,199,865.

The invention described herein relates to springs and spring appliances. More specifically, it relates to a spring tensioning device which is releasable in response to a predesigned tension force. One particularly useful application of the device is in the field of orthodontics.

In orthodontics it is frequently necessary to move teeth along the jaw so as to assure proper spacing and correct malocclusions. This movement is termed retraction. Retraction of individual teeth in orthodontic treatment is accomplished by various mechanisms and techniques. The ideal retraction mechanism would be one that applies a force no greater than the capillary pressure of the peridontal membrane. No practical force mechanism is available that creates a constant force of this minute magnitude. However, it is generally accepted that the bodily retraction of a tooth without severe loss of anchorage is best accomplished with light forces.

The design of fixed orthodontic appliances and the oral environment combine to restrict the retraction mechanisms to a limited number of forms or techniques. One important restriction is the distance over which the activated retraction mechanism can provide the requisite retraction force. Ideally, a single activation would retract an individual tooth the total required distance with a continuous uniform light force. In actual practice it has heretofore been difficult to apply the necessary force in anything approaching a constant manner over the entire distance a tooth is moved. Other important considerations in the design of retraction mechanisms are the ease of placement and removal and the ability to withstand the forces of mastication without breakage or deformation. An additional consideration is the desirability of eliminating patient responsibility for activation or placement of the mechanism. Finally, it should be an intra-oral device.

Prior art intra-oral retraction mechanisms include closed coil metallic springs, open coil metallic springs, and elastic materials. Elastic bands of certain rubbers or plastics have several advantages insofar as they can be inserted and removed by the patient, do not have to be cleaned because they are disposable, and do not have to be reactivated by the orthodontist. Unfortunately, they also have a number of rather severe disadvantages. The fact that they can easily be removed by the patient at will serves to frustrate the orthodontist's efforts if they are in fact prematurely removed. More importantly, presently used elastic materials are subject to interaction with the natural fluids in a patient's mouth. This interaction rapidly degrades the physical properties of the conventional strand elastics, resulting in a tensile force reduction of about 40% after the elastics have been in place for only a few hours. Accordingly, the restoring force exerted by the elastic when stretched to a specific elongation does not remain constant and is difficult to control. For this reason, elastic bands require frequent replacement.

Coil springs of metal wire or other spring material are used as retraction mechanisms by attaching them in tension between a fixed anchor point in the mouth and the tooth desired to be moved. The tension expands or opens the coils of the spring and the retractive force is produced by the coils attempting to close to the rest position. It will be apparent that as the retracting tooth moves, the coils approach nearer to the rest position and, as a result, the force acting on the tooth is reduced.

Compression springs are formed from open coil metallic or other spring material and operate just the reverse of tension springs. In operation, they are placed in compression so that the coils supply a force by attempting to move back to the open, rest position. As a practical matter in orthodontics, compression springs are not as frequently used for retraction, although some orthodontists do use them for this purpose.

The standard retracting springs are normally closed coil tension springs with straight wires at either end which are used to mount them to brackets on an anchor tooth and the tooth to be retracted. Tying these ends to the brackets is often a difficult procedure, especially in the back of the mouth. It is also time consuming. Removal is also time consuming, requiring in the usual practice that the spring coils be cut and the ends then unwrapped from the brackets on the teeth. In the back of the mouth this unwrapping may inadvertently result in puncture wounds in the cheek or gum because the wire normally is of small diameter and readily penetrates tissue. In any case, the process is normally uncomfortable to the patient.

It will be apparent that it is highly desirable to minimize or avoid tying or wrapping procedures altogether—particularly in the back of the mouth—while at the same time assuring that the retracting spring is not capable of being readily removed by the patient.

In U.S. Pat. No. 3,936,938 for "Orthodontic Spring Appliance and Spring Clip Therefor" issued on Feb. 10, 1976, the inventor discloses apparatus for avoiding the wrapping problem. In this apparatus, at least one end of the retraction spring has a straight extension with protrusions spaced at predetermined intervals. The wire with protrusions may be readily connected to a spring clip which may be attached to the arch wire or a tooth bracket. The clip has a slot therein which is so designed that it readily accommodates the protrusion but prevents the wire from being pulled out by the tension force of the spring. For the clip to be effective, however, the protrusion must be such that it does not deform and pass through the clip when normal tension forces are applied to the spring.

It should be noted that the spring appliance of U.S. Pat. No. 3,936,938 requires the use of a special spring clip which appears to have no utility other than as an anchor point for the retraction spring. Further, spring clips of the type disclosed in this patent are subject to occasional inadvertent release of the spring. They also permit the patient to easily release the spring. In either instance, the purpose of the orthodontist is nullified.

SUMMARY OF THE INVENTION

The present invention encompasses a tensioning device which provides a tension spring for exerting a force between two objects and an integral tension releasable member. The tension releasable member serves to hold one end of the tension spring in a force exerting position relative to one of the objects. The tension releasable member is designed to respond to a predetermined force by undergoing deformation and thereby releasing one end of the tension spring. The invention further contemplates a double action retraction coil spring where a tension spring and a compression spring are formed into an integral unit. The compression spring at least partially overlies the tension spring and engages a restraining device so that whenever the tension spring is under tension the compression spring is under compression. The combination tension-compression spring may also be tension releasable and provides for a greater degree of elongation from a constant force than a conventional single acting spring. A particularly useful application of the invention is in the field of orthodontics as a device to apply a repositioning force to a tooth to be moved. The invention also encompasses an orthodontic method of exerting a retraction force on a tooth to be repositioned. The method employs tension and compression forces simultaneously and also provides for the tensioning force to be releasable at a predetermined value.

Figure 1:
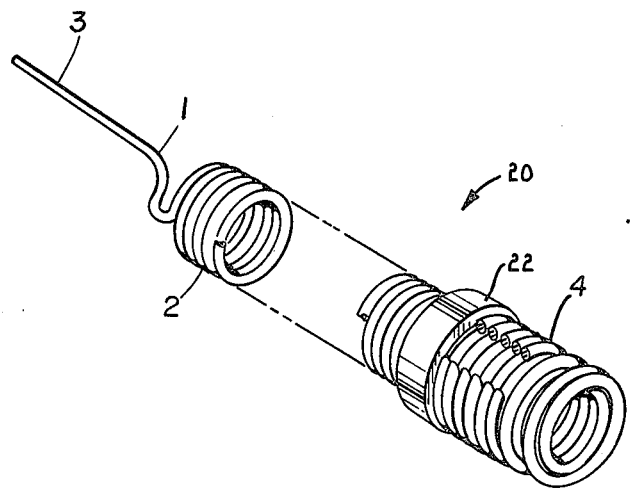
FIG. 1 is a perspective view of one embodiment of the spring appliance of this invention.

It is therefore a primary object of the present invention to provide a tension device having an integral tension releasable portion which will respond to a predetermined force to release the tension device.

As a corollary to the above object, an important objective is to provide a tension releasable tensioning device which is easily installed in areas with poor accessibility and can be removed by applying the predetermined force factor which will cause deformation of the releasable portion.

Another corollary of the first mentioned object is to provide a tension device of the type described which offers a safety factor against excessive tension forces by being tension releasable.

A further important objective of the invention is to provide a unitary tensioning device which comprises in combination a spring tensioning member and an integral compression spring member which extends partially around the tensioning member thereby providing simultaneous tensioning and compression forces.

As a corollary to the preceding objective, an aim of the invention is to provide a spring tensioning device having greater elongation than a spring of the same length and design having only the tensioning member.

As another corollary for the above objective, an aim of the invention is to provide a spring assembly which is particularly useful in orthodontics because of its ability to maintain a relatively constant force over a greater distance than a conventional spring.

A further objective of the invention is to provide an orthodontic spring which is tension releasable thereby being particularly useful in areas with poor accessibility making it difficult to wrap or unwrap a conventional type of spring.

An important goal of the invention is to provide an orthodontic method of applying a tensioning force through the use of a tension spring having an integral tension releasable device which facilitates placement and removal of the assembly.

A further object of the invention is to provide an orthodontic method of the type described wherein the tensioning means is countered with a compression yieldable member thereby providing for greater elongation than is possible using a comparably designed tension member alone.

Other objects of the invention will be made clear or become apparent from the following description and claims when read in light of the accompanying drawing.

DESCRIPTION OF THE PREFERRED EMBODIMENTS

Proper selection of spring material and the configuration of it is important in the manufacture of all embodiments of the invention. Spring tempered wire stock is commercially available with satisfactory strength and elastic properties for most applications. For orthodontics, stainless steel should be utilized. Knowing the basic physical properties of a particular wire, the determination of spring parameters such as wire diameter, length of coil, and coil diameter is readily made by referring to any of the standard texts on spring design. Other acceptable spring materials for certain applications include hard rubber and plastics. These are only exemplary and are not intended to be exhaustive of all materials which may find application in the present invention.

To be functional and comfortable for orthodontic use, the coil springs of this invention should have a sufficiently small outside diameter so that they can be accommodated in the limited space available in the vestibules of the mouth. Moreover, the springs should also be available in various lengths to permit use in a variety of positions and to accommodate the wide ranges of intra and intermaxillary spans in the mouths of different patients. Appliance length is readily determinable because other parameters such as wire diameter, cross section, and material, coil diameter, and the number of springs can be varied to provide a spring having a desired unelongated or static length and a desired working elongation.

In most instances, the tensioning portion of the assembly of the invention will be provided by a coil tension spring, although other types of spring tensioning devices may be employed. In the orthodontic field, the tension spring is preferably of the closed coil type, i.e. each coil is contiguous with an adjacent coil when the spring is at rest.

When the invention is used in orthodontics, appropriate fixed spring mounting means is used to hold the tensioning device once the tension spring is activated to the desired tension. Typically, such fixed spring mounting means is attached directly to an anchor tooth but this need not automatically be the case. Thus, it could be attached to the arch wire at an appropriate point. The anchor portion of the device of the present invention is tension releasable, i.e., it releases from the passes through the mounting means when sufficient force is applied to the tension spring. This permits the orthodontist or a technician acting under his direction to easily remove the spring from the mounting means merely by firmly pulling on the spring. In one embodiment of the invention, the anchor portion is a plurality of enlarged closed coils of the spring wire formed at the end of the tension spring. Preferably, the enlarged anchor coils are formed over a portion of the tension spring. The diameter of the outer closed anchor coils is sufficiently large that it engages the mounting means firmly while yet permitting the inner tension spring to pass therethrough.

In another embodiment, which is the preferred embodiment, the anchor coils comprise an open coil spring which is compressed when the closed tension spring is elongated and thus serves to produce a retractive force along with that resulting from the elongation of the tension spring. This latter embodiment is conveniently characterized as a double action retraction coil spring. One of the advantages of the double action retraction spring is that it has a greater elongation factor for a given force than a comparable simple spring. This offers advantages in many applications where it is desired to flex the spring over the maximum distance. For example, in orthodontics a more constant force may be placed on a retracting tooth for a longer perior of time (and thus over a greater distance) than with a conventional spring. This provides for better retraction with less spring adjustment.

Figure 4:
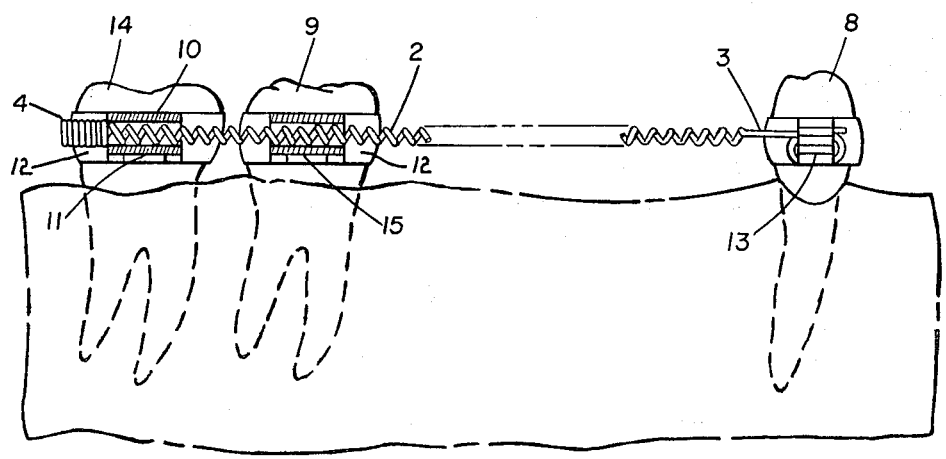
FIG. 4 is a side elevational view of the orthodontic assembly of the invention showing the use of the spring appliance in a limited working space.
Figure 5:
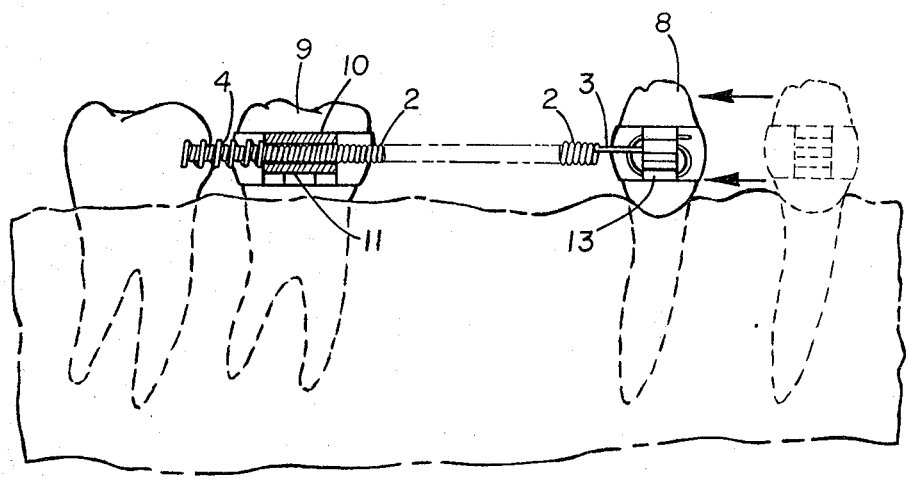
FIG. 5 is a side elevational view showing the retractive effect after the assembly of FIG. 3 has been in use for a period of time.

Another substantial advantage of the present invention over the teaching of the prior art is that it permits retractions in limited working areas such as that shown, for example, in FIG. 4. Most prior art coil springs are designed to be placed in a region located adjacent the spacing between the teeth involved. With the present invention, however, a portion of the spring is located adjacent the anchor tooth because it passes through the mounting means positioned on the side of the anchor tooth. This increases the effective available working distance for the spring.

With appropriate modification, the spring clips disclosed in U.S. Pat. No. 3,936,938 may be used as the rear mounting means for the retraction spring. U.S. Pat. No. 3,936,938 is hereby incorporated by reference into this application. Preferably, however, a variety of commerically available buccal tubes, e.g., headgear tubes, twin-wire tubes, lightwire tubes, and the multiphase maxillary and mandibular tubes, may conveniently be used for this purpose. It can be seen that the use of buccal tubes is advantageous in that such tubes serve to protect a substantial portion of the closed coil spring. It does not matter whether the cross section of the buccal tube is circular, square, or rectangular, provided that the diameter of the tube is sufficient to permit the inner closed coil portion of the spring to pass readily therethrough while at the same time preventing the outer anchor coil from so doing.

The spring device of the invention may be easily attached to the tooth to be retracted by wrapping a straight wire extension or tail from the spring coil around a bracket on this tooth. This is a technique well known and commonly used in the orthodontic art. See, e.g., FIG. 3. Alternatively, spring clips and spring tails of the type taught in U.S. Pat. No. 3,936,938 may be used for this purpose.

One embodiment of the unitary tension producing appliance of the invention is shown in FIG. 1 and designated generally by the numeral 20. Any metallic or non-metallic spring material may be used for forming appliance 20 although it is preferable to use a single strand of spring tempered wire 1. Wire 1 is formed into a first tension responsive spring section such as closed coil spring 2. A straight extension or tail 3 provides means for securing one end of the spring to an object. Integral with spring 2 and formed from a continuation of wire 1 is an anchor spring 4. Anchor spring 4 is also a closed coil spring and extends around and back over coil spring 2 thereby presenting a larger outside diameter than that of the first mentioned spring. Anchor spring 4 is intended to bear against some type of rigid retainer such as collar 22. Collar 22 is affixed to an object to which tension forces are to be applied. The collar at least partially circumscribes spring 2 and forms a stop for spring 4. The number of "turns" in anchor spring 4 is carefully selected so that the anchor spring is deformable upon application of a predetermined force to tail 3. That is, with anchor spring 4 in engagement with collar 22, once the design maximum force is reached anchor spring 4 will be deformed and pass through collar 22 thereby releasing spring 2.

The number of turns in anchor spring 4 and their diameter will determine the amount of force required to deform the spring. There should be a sufficient number of turns so that the anchor coil 4 will not deform and release the spring 2 prematurely below the proportional limit of the tension spring and preferably not until this limit has been reached or exceeded. On the other hand, the number of turns (i.e. 360 degree revolutions) should not be so great that excessive force is required to deform the anchor coil.

Figure 2:
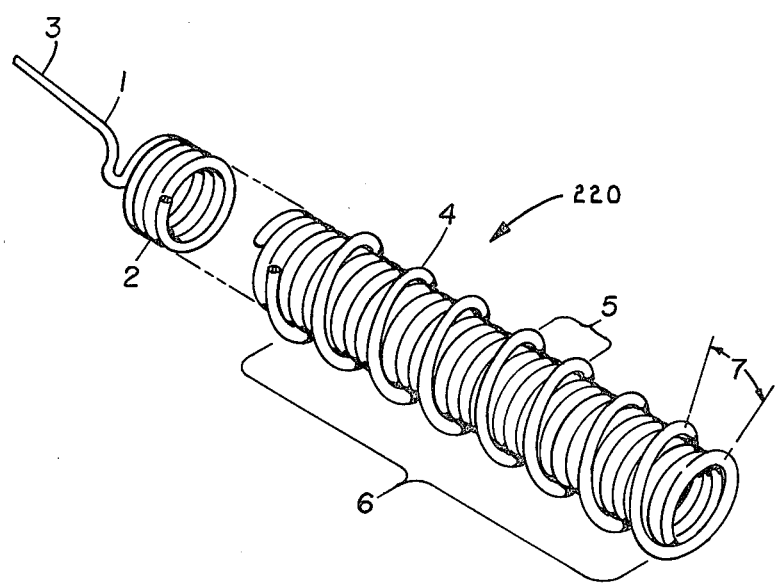
FIG. 2 is a perspective view of a preferred embodiment of the spring appliance of the invention.
Figure 6:
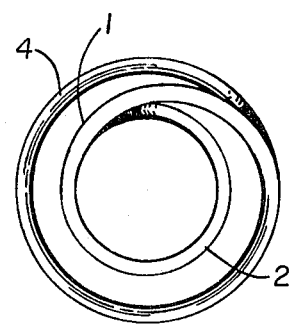
FIG. 6 is an end elevational view of the spring of FIG. 2.

The preferred embodiment of the unitary tensioning device of the invention is designated generally by the numeral 220 and shown in FIG. 2. The device 220 is substantially similar to the device 20 and includes a tension responsive closed coil 2 formed from wire strand 1. In this embodiment, however, anchor coils 4 are separated by space 5 so as to present an open coil compression responsive spring 6. As shown in FIG. 6, the inside diameter of open coil compression spring 6 is sufficiently larger than the outside diameter of tension spring 2 that the two coils may move freely relative to one another.

As with the device 20 previously described, device 220 is designed to be used in conjunction with a collar 22 (not shown in FIG. 2) or other restraining device against which anchor coil 6 compresses. Whenever spring 2 of the embodiment 220 is under tension and spring 6 is in engagement with some restraining device, the spring 6 will be under compression. Thus, the embodiment 220 forms a double action retraction coil spring. As with the embodiment 20, the anchor coils 4 are deformable when the tension force on spring 2 exceeds a predetermined value. The same factors discussed above with regard to the embodiment 20 are applicable in designing the spring 6 to deform at a predetermined value. In addition to the number of turns and the diameter of the coils, the pitch 7 of the spiral formed by the coils of the spring 6 is another variable affecting the force required for deformation.

Figure 3:
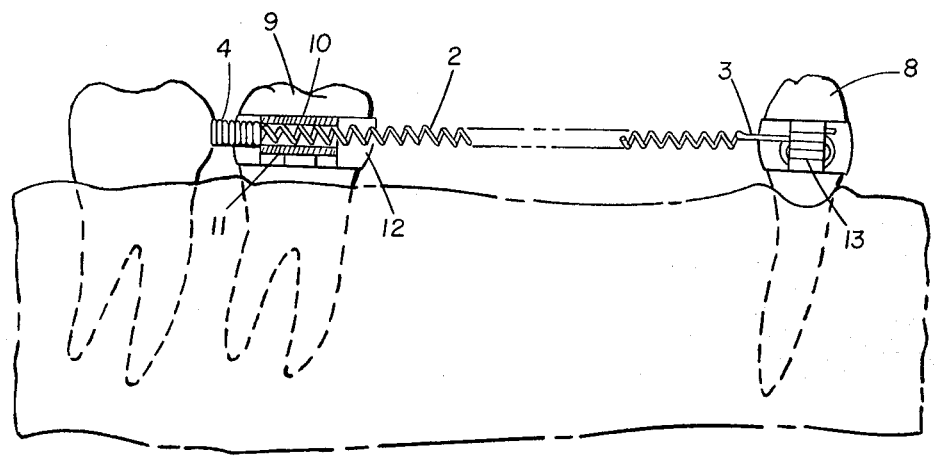
FIG. 3 is a partially cut-a-way side elevational view of one embodiment of the orthodontic assembly of the invention.

FIG. 3 shows one application of the tensioning device of the invention. In FIG. 3, mounting means 10 is a buccal tube 11 attached to band 12 on anchor tooth 9, but as has been indicated previously in the specification, it could as easily be a spring clip of the type disclosed in U.S. Pat. No. 3,936,938 modified to permit the passage of coil 2 therethrough. The appliance is activated as follows. The tail 3 of the spring is passed through buccal tube 11 from the distal to the mesial end, i.e., from the end of the tube furthest from the tooth 8 to be retracted to the end closest to that tooth. Coil 2 is pulled through tube 11 until anchor coil 4 butts against the distal end of tube 11. Buccal tube 11 thus holds coil 2 in place and protects a substantial portion of it from deformation. The spring appliance is activated by pulling on tail 3 to extend closed coil 2. If the embodiment of FIG. 2 is used, this pull simultaneously compresses open coil 6 which is also serving as anchor coil 4. When the desired force is present, the tail 3 is attached to the tooth 8 desired to be retracted in such a manner that this force is then maintained on that tooth. This is easily accomplished by wrapping tail 3 around a bracket 13 on tooth 8 and snipping off the excess.

As the retraction progresses, the spring gradually relaxes to its inactivated or rest state as shown in FIG. 8. When the retraction is complete or when another spring is desired to be used, the spring in place is readily removed by cutting tail 3 near coil 2 and then pulling the spring forward through tube 11 with a force sufficient to exceed the design maximum of anchor coil 4. This causes anchor coil 4, which heretofore had been holding the spring in place in tube 11, to uncoil into and through the tube 11. The remaining portion of tail 3 is quickly and easily unwrapped from bracket 13 on tooth 8.

In the application illustrated in FIG. 4, tooth 9 is used to mount a buccal tube 15 attached to band 12. An adjacent tooth 14 mounts buccal tube 10 and serves as the anchor tooth. Buccal tube 15 encases a portion of spring 2 thereby supporting it from deflection.

Although the spring appliance or assembly of FIGS. 3 and 4 is directed to the retraction of teeth, it will be apparent that what is in general disclosed and shown in these figures is a tensioning device which comprises in combination (a) a tension portion such as closed first coil 2, (b) an enlarged tension releasable portion such as open second coil 6 with the second coil having an internal diameter greater than the external diameter of first coil 2 and with first coil 2 located at least partially within second coil 6, (c) first retaining means such as 13 for holding first coil 2 in tensioned engagement with a workpiece 8 desired to be acted upon by the spring, and (d) second tubular retaining means such as 11 for engaging the end of second coil 6 not connected to first coil 2 to produce compression in second coil 6 when first coil 2 is placed in tension. The device will find application in many areas besides the orthodontic field herein specifically described.

From the foregoing, it will also be appreciated that the present invention encompasses a novel method of orthodontic treatment. The method comprises anchoring one end of a tension spring to an anchor point in the mouth, placing the spring under tension, securing one end to a tooth to be repositioned, and providing a tension releasable device in conjunction with the tension spring. The tension releasable means should be characterized by an ability to undergo deformation when the force on the tension spring exceeds a predetermined design maximum. Preferably, the step of providing a tension releasable device will include providing a compression spring in conjunction with the tension spring. Thereby, the tension force will be countered by a compression force up to the design limit of the tension releasable compression spring.

I claim:

1. A unitary tension producing article of manufacture for exerting a tension force between two objects, one of said objects being provided with a stop for said article, said article comprising:
   tension spring means;
   means for coupling one end of said spring means with one of said objects;
   anchor means comprising an integral extension of said spring means and extending in at least partially overlying relationship to said tension spring means, said anchor means being biased against said stop by said spring means and characterized by being resiliently yieldable under the influence of said spring means while holding the other end of said spring means and deformable when the force exerted by said spring means exceeds a predetermined value thereby causing said anchor means to move past said stop and release said spring means from said other object.

2. The invention of claim 1, wherein said tension spring means comprises a coil spring.

3. The invention of claim 1, wherein said anchor means comprises an open coil spring.

4. The invention of claim 1, wherein said tension spring means comprises a closed coil spring.

5. The invention of claim 1, wherein said predetermined value is at least equal to the proportional limit of said spring means.

6. A double action coil spring which comprises a single continuous strand of spring material formed into a first tension responsive coil spring and a second compression responsive coil spring, said second coil having an internal diameter greater than the external diameter of the first coil and extending at least partially along the length of said first coil, said second coil adapted to engage a restraint and characterized by being resiliently yieldable under the influence of said first coil while holding the latter in place and deformable in response to a predetermined force exerted through said first coil whereby when said force is achieved said second coil moves past said restraint to release said first coil.

7. The invention of claim 6, wherein said first spring comprises a closed coil spring.

8. The invention of claim 7, wherein said second coil is disposed substantially only around said first coil.

9. An orthodontic treatment assembly for applying repositioning forces to a tooth in a patient's mouth, said assembly comprising:
   tension spring means;
   means for coupling one end of said spring means with a tooth;
   anchor means comprising an integral extension of said spring means and extending in at least partially overlying relationship to said tension spring means; and
   means coupled with another tooth and adapted to be engaged by said anchor means,
   said anchor means being biased against said means coupled with another tooth by said tension spring means and characterized by being resiliently yieldable under the influence of said spring means while holding the other end of said spring means and being deformable when the force exerted by said tension spring means exceeds a predetermined value thereby causing said anchor means to move past said means coupled with another tooth and release said spring means.

10. The invention of claim 9, wherein said means coupled with another tooth comprises a buccal tube and said anchor means comprises coil spring means.

11. The invention of claim 9, wherein said tension spring means comprises a closed coil spring.

12. The invention of claim 11, wherein said anchor means comprises an open coil spring which is under compression whenever said tension spring means is under tension.

13. A method of releasably holding a tension spring between a tooth and a fixed member, said method comprising the steps of:
  anchoring one end of said tension spring to one of said fixed member or said tooth;
  placing said spring means under tension whereby to exert a tension force on said tooth;
  providing compression spring means integral with said tension spring means and extending partially along the length of said tension spring means;
  providing means secured to the other of said fixed member or said tooth for holding said compression spring means; and
  exerting a force on said tension spring to place said compression spring under compression while the compression spring holds said tension spring in place.

14. A method as set forth in claim 13, wherein said compression spring means is characterized by an ability to undergo deformation when the force on said tension spring means exceeds a predetermined design maximum thereby releasing said compression spring means from said mounting means.

15. A method of releasably holding a tension spring between a tooth to be repositioned and a fixed member, said method comprising the steps of
  anchoring one end of said tension spring to one of said fixed member or said tooth;
  placing said tension spring means under tension whereby to exert a tension force;
  countering said tension force with a compression spring integral with said tension spring, which compression spring extends in at least partially overlying relationship to said tension spring; and
  providing means secured to the other of said fixed member or said tooth against which said resilient anchor member acts to undergo limited yielding movement under the influence of said tension spring while holding the other end of said tension spring means.

16. A method as set forth in claim 15, wherein said step of providing means fixed to said other tooth comprises providing tubular means having an inside dimension larger than the corresponding dimension of said tension spring means and smaller than said compression spring means.

17. A method as set forth in claim 15, wherein said compression spring is characterized by an ability to undergo deformation when the force exerted by said tension spring exceeds a predetermined design maximum thereby releasing said compression spring means from said means secured to the other of said fixed member or said tooth.

18. A unitary tension producing article of manufacture for exerting a tension force between two objects, one of said objects being provided with a stop for said article, said article comprising:
  tension spring means;
  means for coupling one end of said spring means with one of said objects;
  anchor means comprising an open coil spring which is an integral extension of said tension spring means and extending at least partially along the length of said tension spring means,
  said open coil spring being biased against said stop by said tension spring means and characterized by being resiliently yieldable under the influence of said tension spring means while holding the other end of said tension spring means and being deformable when the force exerted by said tension spring means exceeds a predetermined value thereby causing said open coil spring to move past said stop and release said tension spring means from said other object.

* * * * *